(12) United States Patent
Friedrich et al.

(10) Patent No.: US 9,709,179 B2
(45) Date of Patent: Jul. 18, 2017

(54) DEVICE FOR CONTROLLING FLUID FLOWS IN LAB-ON-A-CHIP SYSTEMS

(71) Applicant: Boehringer Ingelheim Vetmedica GmbH, Ingelheim am Rhein (DE)

(72) Inventors: Katja Friedrich, Nürnberg (DE); Walter Gumbrecht, Herzogenaurach (DE); Peter Paulicka, Röttenbach (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

(21) Appl. No.: 14/834,870

(22) Filed: Aug. 25, 2015

(65) Prior Publication Data
US 2016/0051984 A1    Feb. 25, 2016

Related U.S. Application Data

(62) Division of application No. 13/375,191, filed as application No. PCT/EP2010/055817 on Apr. 29, 2009, now Pat. No. 9,151,409.

(30) Foreign Application Priority Data

May 29, 2009 (DE) ........................ 10 2009 023 430

(51) Int. Cl.
*F16K 11/065* (2006.01)
*F16K 11/16* (2006.01)
(Continued)

(52) U.S. Cl.
CPC ...... *F16K 11/065* (2013.01); *B01L 3/502738* (2013.01); *F16K 7/16* (2013.01);
(Continued)

(58) Field of Classification Search
CPC ............ F16K 99/0059; F16K 99/0061; F16K 99/0026; F16K 2099/0084;
(Continued)

(56) References Cited

U.S. PATENT DOCUMENTS 1,796,644 A    3/1931   Carrington
2,914,629 A   11/1959   D'Aprile et al.
(Continued)

FOREIGN PATENT DOCUMENTS

DE    2 107 437 A    10/1971
DE    600 00 109 T2   11/2002
(Continued)

OTHER PUBLICATIONS

International Search Report for PCT/EP2010/055817; mailed Aug. 30, 2010.

*Primary Examiner* — Atif Chaudry
(74) *Attorney, Agent, or Firm* — David S. Safran

(57) ABSTRACT

An array of valves are arranged in n columns and m lines and which are each designed to control a fluid flow in an associated flow channel in a lab-on-a-chip system. The array includes at least two valves, every column having not more than one valve and every line having from zero to n valves. A device is used for actuating the valves. The valves are pressure-actuated. To produce the device, the flow channels are arranged in accordance with the arrangement of the valves. Which valves are actuated being changeable by movement of projections relative to array of valves so as to change which valves the projections are pressed against.

19 Claims, 1 Drawing Sheet

(51) Int. Cl.
*F16K 7/16* (2006.01)
*F16K 27/00* (2006.01)
*F16K 31/524* (2006.01)
*F16K 99/00* (2006.01)
*G01N 35/00* (2006.01)
*B01L 3/00* (2006.01)
*G01N 35/10* (2006.01)

(52) U.S. Cl.
CPC .......... *F16K 11/161* (2013.01); *F16K 27/003* (2013.01); *F16K 31/52483* (2013.01); *F16K 99/0001* (2013.01); *F16K 99/0015* (2013.01); *F16K 99/0042* (2013.01); *G01N 35/1097* (2013.01); *B01L 2300/0636* (2013.01); *B01L 2300/0816* (2013.01); *B01L 2300/123* (2013.01); *B01L 2400/06* (2013.01); *B01L 2400/0655* (2013.01); *B01L 2400/0661* (2013.01); *B01L 2400/082* (2013.01); *F16K 2099/008* (2013.01); *F16K 2099/0084* (2013.01); *G01N 2035/00158* (2013.01); *G01N 2035/00237* (2013.01); *Y10T 137/0396* (2015.04); *Y10T 137/86445* (2015.04); *Y10T 137/86919* (2015.04); *Y10T 137/87* (2015.04)

(58) Field of Classification Search
CPC ....... F16K 31/52475; F16K 31/532483; F16K 31/52491; F16K 11/074; F16K 11/065; F16K 11/0655; F16K 27/003; F16K 27/044; F16K 7/16; F16K 11/161; Y10T 137/86919; Y10T 137/87; Y10T 137/86445
See application file for complete search history.

(56) References Cited

U.S. PATENT DOCUMENTS

| | | |
|---|---|---|
| 3,566,921 A | 3/1971 | Bell et al. |
| 3,613,729 A | 10/1971 | Dora |
| 4,006,753 A * | 2/1977 | Ingram, Jr. ............... F16K 7/16 137/607 |
| 4,601,881 A | 7/1986 | Webster |
| 4,852,551 A | 8/1989 | Opie et al. |
| 5,472,169 A | 12/1995 | Forney et al. |
| 5,927,332 A | 7/1999 | Richard |
| 5,932,799 A | 8/1999 | Moles |
| 6,994,314 B2 | 2/2006 | Garnier et al. |
| 7,601,270 B1 | 10/2009 | Unger et al. |
| 9,151,409 B2 * | 10/2015 | Friedrich .......... B01L 3/502738 |
| 2002/0029814 A1 * | 3/2002 | Unger ............... B01L 3/502707 137/824 |
| 2010/0093559 A1 | 4/2010 | Fan et al. |

FOREIGN PATENT DOCUMENTS

| | | |
|---|---|---|
| EP | 0 002 173 A1 | 6/1979 |
| EP | 0 180 064 B1 | 5/1986 |
| EP | 0 420 296 A1 | 4/1991 |
| GB | 1 243 435 A | 8/1971 |
| JP | 61-110028 A | 5/1986 |
| JP | 2002-282682 A | 10/2002 |
| JP | 2007-085537 A | 4/2007 |
| WO | 2008/121691 A1 | 10/2008 |

\* cited by examiner

DEVICE FOR CONTROLLING FLUID FLOWS IN LAB-ON-A-CHIP SYSTEMS

CROSS REFERENCE TO RELATED APPLICATION

This application is a continuation of commonly owned, co-pending U.S. patent application Ser. No. 13/375,191, filed Nov. 29, 2011, which is a §371 of PCT/EP2010/055817 filed Apr. 29, 2010 which claims the benefit of German Application No. 102009023430.6 filed on May 29, 2009, the benefit of both of which is claimed and both of which are incorporated by reference herein in their entirety.

FIELD OF THE INVENTION

Described below is a device for controlling fluid flows in lab-on-a-chip systems, using an array of valves. The valves are arranged in n columns $S_n$ and m rows $Z_m$, n and m being integers. They are each configured to control a fluid flow in an associated flow channel. The device furthermore includes an instrument for actuating the valves. A device having the features described above is known, for example, from European Patent EP 0 180 064 B1 and corresponding U.S. Pat. No. 4,601,881. Also described below are methods for controlling fluid flows in such lab-on-a-chip systems and to methods for producing the device.

DESCRIPTION OF RELATED ART

In biosensor technology, lab-on-a-chip systems are used in order to be able to carry out biochemical analyses in parallel. Microfluidic instruments and a chip having an array of sensors are integrated on a support, which for example may be a plastic card. The array of sensors may, for example, be formed by electrochemical sensors which are arranged in columns and rows on the chip. The sensors are coated with molecules, to which the substances to be detected bind specifically. The specific binding is detected electrochemically by changes in current and/or voltage. In this way, biochemical substances, for example antibodies, peptides or DNA, can be detected in solutions to be examined, for example blood or urine.

The measured electrochemical signals may be processed directly by integrated circuits on the chip, or they may be read out from the chip by an external evaluation unit. The chemicals required for the examination may be delivered from the external evaluation unit to the support or they may already be on the support, for example in the form of dry reagents. During the examination, the solutions i.e. liquids are delivered to the support and fed on the support via microchannels into a reaction chamber. The chip with the sensor array is located in the reaction chamber. Reactions required for the detection may take place in the microchannels and/or the reaction chamber.

In the case of complex biochemical reactions which are required for the detection, the fluid flow of the solution must be controlled. For instance, it may be necessary for the liquid to stay for a predetermined period of time in a region of the microchannels, so that for example dry reagents which are stored in this region are dissolved and chemical reactions can take place. Only after completion of the chemical reactions is the liquid fed further through the microchannel. Furthermore, when detecting biochemical substances in the reaction chamber it may be necessary to close the reaction chamber in a fluid-tight fashion. To this end, valves are to be provided in the support. They are to be arranged at particular selected positions in the support, for example in the inlet and outlet of the reaction chamber.

EP 0 180 064 B1 and corresponding U.S. Pat. No. 4,601,881 disclose a valve array of valves which are designed to close microchannels. The microchannels are arranged in a first support, which is covered with a thin membrane on one side of the microchannels. The thin membrane is arranged in a sandwich fashion between the first support and a second support. Arranged in the second support, there are plunger-like instruments which can be pressed with the aid of springs via the membrane onto openings of the microchannels in the first support. The microchannels are thereby closed by the membrane. The described valves are arranged according to the position of the flow channels on the support. They are driven individually and separately from one another.

In the case of complex analysis processes, it is indispensable to carry out a plurality of chemical processes separately from one another simultaneously on a chip card. To this end, a plurality of valves of an array of valves on the chip card must be actuated simultaneously. Systems in the known art, as described for example in EP 0 180 064 B1, individually control the valves separately from one another, which is very complicated and leads to high costs.

SUMMARY OF THE INVENTION

Described below is a device having an array of valves, in which the valves can be controlled simultaneously with a simple and economical structure. Also described below is a method which allows control of the valves simultaneously according to a set program without elaborate electronics and individual electrical driving of the valves. Also described below is a method for producing the array of valves, which starts on the basis of the arrangement of the valves.

The device for controlling fluid flows in lab-on-a-chip systems has an array of valves, the valves being arranged in n columns $S_n$ and m rows $Z_m$. In this case, n and m are integers. The array includes at least two valves, each column $S_n$ having no valve or at most one valve and each row $Z_m$ having between zero and n valves. The valves are each configured to control a fluid flow in an associated flow channel. The device furthermore includes an instrument for actuating the valves.

The special arrangement of the valves in the array makes simple control possible. In each column, there is only one valve. By virtue of an arbitrary number of valves in the rows, however, it is possible to achieve any required valve arrangement since the number of columns and the number of rows are freely selectable. The array of valves can be designed according to the requirements of the chemical processes to be controlled and therefore the fluidics in an analysis or examination, and the time profile of the processes, in particular processes taking place simultaneously at different positions. The fluidic channels and chambers are arranged in accordance with the design of the array of valves. The arrangement of the valves in array form permits particularly simple production, adaptable for many processes or reproducible, of the device.

The instrument for controlling the valves may have an essentially plane plate having elevations projecting from the plane, in which n' columns $S_{n'}$ and m' rows $Z_{m'}$ are arranged. The spacings of neighboring columns $S_{m'}$ may in this case be equal to the spacings of associated neighboring columns $S_n$ of the valves.

The instrument for controlling the valves permits mechanical control of all valves simultaneously according to a set program. Its structure in n' columns $S_{n'}$ and m' rows $Z_{m'}$ makes it compatible with the array of valves.

By mounting the essentially plane plate movably in a first direction relative to the array of valves, the first direction extending parallel to the columns $S_n$ of the array of valves, valves can be controlled by moving the essentially plane plate. The elevations projecting from the plane of the plate may in this case on the one hand be arranged in n' columns $S_{n'}$ and m' rows $Z_{m'}$ so that individual valves are closed or opened in a controlled way according to a predetermined program during a movement of the essentially plane plate along the first direction relative to the array of valves.

Since only one valve is arranged in each column $S_n$ of the array of valves, during movement of the plate along the gap an elevation in the essentially plane plate controls only this one valve. Depending on the spacing and number of elevations, the one valve can be opened and closed. A plurality of elevations in a row lead to simultaneous actuation of valves arranged in a row. The arrangement of the valves and the elevations therefore determines the program according to which the valves are controlled. With a predetermined arrangement of the valves in the array, the program can be determined by arrangement of the elevations.

The array of valves may be arranged in a chip card, the chip card including a flat body made of a plastic material in credit card form, on a front side of which a film is applied, in particular a self-adhesive film. In the body, on the surface of the front side, flow channels may be arranged as recesses, as well as the valves which contain an elastomer compound that is arranged at least partially next to a respectively associated flow channel. This provides a particularly simple and economical to produce structure of the array of valves, especially since chip cards are common in biosensor technology and can therefore be used in standard instruments. This likewise reduces costs, because it is not necessary to develop an entirely new concept of the analysis instruments.

The plastic body may be formed of polycarbonate or polypropylene. The elastomer may be a thermoplastic elastomer, in particular rubber or a mixture of polypropylene and ethylene propylene diene M-class elastomer. These materials are easy to process and economical. They are also inert with respect to most chemicals used in biosensor technology. These materials furthermore do not react, or react only to a small extent, with the substances to be analyzed. Changes in the folding of the substances or molecules or other reactions, which vitiate the examination, generally do not take place as a result of these materials.

The chip card may be arranged in a sandwich fashion in the instrument for actuating the valves. On a rear side of the chip card, a plunger for actuating the respective valve may respectively be arranged in an instrument plate, the plunger being prestressed by at least one spring between the instrument plate and the plunger so that essentially no pressure force exists between the plunger and the valve. The mechanically more complicated and therefore more cost-intensive part is therefore fitted in the instrument for actuating the valves. For a disposable chip card to be used once, it is thus possible to employ inexpensive materials without an elaborate production process.

The sandwiched arrangement of the chip card in the instrument for actuating the valves leads to secure and positionally stable mounting, so that the chip card does not slip relative to the instrument. This ensures that the plunger can reliably actuate the associated valve at any time. A reliable functionality is thereby ensured.

A method for controlling a device as described above includes actuation of the valves respectively by application of a pressure force, which is exerted in particular by at least one plunger, on the respective valve. When a pressure force is not applied a valve is opened and a fluid flows in an associated flow channel, and when a pressure force is applied to the valve the valve is closed and the fluid flow is prevented in the associated flow channel.

This method is particularly simple and controls the liquid flow effectively. What is important in this case is that gas- and/or liquid-tight closure of the valve is ensured. The activation by a pressure force permits a simple structure of the valve and the activation action. A reliable functionality without fatigue of the materials is feasible even with frequent opening and closing.

The opening and closing of the valves may be carried out according to a predetermined program by moving the essentially plane plate parallel to the columns $S_n$ relative to the array of valves.

No electrical programming or an elaborate regulating and control loop are necessary. In the case of a frequently executed analysis program which is always the same, this leads to a simple, reliable and economical structure and method. The control of the valves can be carried out exclusively mechanically, by movement of the essentially plane plate. Particularly in connection with the handling of liquids and the laboratory environment, this leads to an increased reliability of the examination owing to less susceptibility to error compared with elaborate control electronics.

The difference between the m' rows $Z_{m'}$ of the instrument for controlling the valves and the m rows $Z_m$ of the array of valves can define the number of process steps in which at least one valve is actuated.

A process involving control of the valves may on the one hand be carried out by moving the essentially plane plate relative to the array of valves with a fixed speed, the duration of a process step being determined by the spacing of the rows $Z_{m'}$ from one another in the case of an equal spacing of all rows $Z_m$ respectively from one another, or the duration of a process step being determined by the spacing of the rows $Z_m$ from one another in the case of an equal spacing of all rows $Z_{m'}$ respectively from one another.

An essentially plane plate can reliably be operated with a constant speed more simply and with less outlay than with accelerated speeds. Drives with a constant speed are economical and reliable. Determining the duration of the process steps by the spacing of the rows leads to a high reproducibility and reliability of the examination.

A process involving control of the valves may on the other hand be carried out by moving the essentially plane plate relative to the array of valves with a speed which is respectively adapted to the duration of a process step, the rows $Z_m$ respectively being arranged equally separated from one another and the rows $Z_{m'}$ respectively being arranged equally separated from one another.

Equal spacings of the rows from one another simplify the structure and production of the device. However, the outlay for driving the essentially plane plate with accelerated movements is greater.

A method for producing a device as described above includes the provision of flow channels in the device as a function of the arrangement of the valves of the array in the n columns $S_n$, and m rows $Z_m$. This permits a design of the device as a function of the valves. Starting with the valves, which are more elaborate to produce, the flow channels and reaction chambers are then arranged or designed. An array of valves can thus be produced simply and economically always with the same array shape by reusing the mold, it only being necessary to establish the positions of the array at which valves are applied or not applied. The channels and chambers, which are less expensive and simpler to produce, are then defined and produced as a function of the valves, the reactions to be carried out and the desired fluidics. Advantages in the costs of the design and the production can thus be achieved in a similar way to semiconductor electronics. In that case, components are arranged on a chip according to the purpose of a circuit and the production technology, and the interconnection is designed and produced according to the position of the components. The components are electrically connected to one another by the interconnection in such a way that the desired electrical circuit is obtained.

The advantages associated with the method for controlling a device and with the method for producing a device are similar to those which were described above in relation to the device for controlling fluid flows in lab-on-a-chip systems.

Preferred embodiments with advantageous refinements will be explained in more detail below with the aid of the figures, but without being restricted thereto.

These and other aspects and advantages will become more apparent and more readily appreciated from the following description of the exemplary embodiments, taken in conjunction with the accompanying drawings of which:

DETAILED DESCRIPTION OF THE INVENTION

Figure 1:
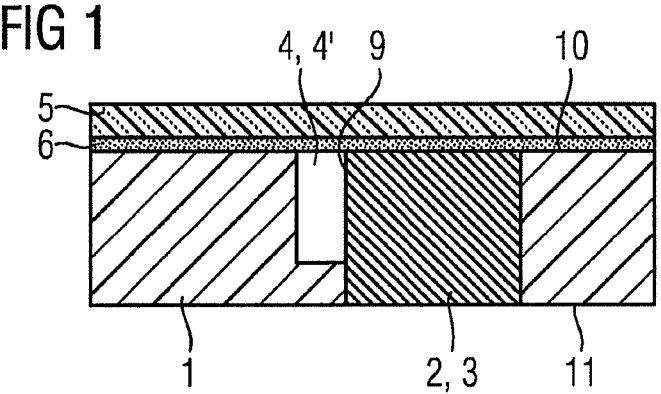
FIG. 1 is a schematic sectional view of the structure of a valve.

Reference will now be made in detail to the preferred embodiments, examples of which are illustrated in the accompanying drawings, wherein like reference numerals refer to like elements throughout.

FIG. 1 shows a valve by way of example for better understanding of the instrument for controlling fluid flows. The valve is constructed from a body 1 made of a plastic material and an elastomer compound 2. The body 1 constitutes a support, or a substrate, and may have the form of a chip card, an electrochemical sensor array for the detection of biochemical substances being arranged on the embedded chip. For the sake of simplicity, the configuration of the chip card will not be discussed in further detail here. Embodiments without a chip are also possible, for example in optical analysis instruments.

A first recess 4 is formed in the support body 1. The first recess 4 is open toward a front side 10 of the support body 1. It has the form of a channel and is used as a flow channel 4'. Liquids or gases can flow through the flow channel 4'. A second recess 3 is formed in direct proximity to the first recess 4, adjacent to the flow channel. It has a common interface with the first recess 4 in a subregion 9 of the first recess 4. The second recess 3, as shown in FIG. 1, is formed continuously from the front side 10 to the rear side 11 of the support body 1. It is fully filled, or occupied, with the elastomer compound 2.

A self-adhesive film 5 is applied flat on the front side 10 of the support body 1. The adhesive layer 6 of the self-adhesive film 5 ensures good adhesion of the film 5 on the support body 1 and on the elastomer compound 2. The film 5 with its adhesive layer 6, in conjunction with the support body 1 and the elastomer compound 2, seals the flow channel 4' from the surroundings in an air- or gas-tight and/or liquid-tight fashion.

In order for the valve to be usable in biochemical devices, the materials which come in contact with the liquids or gases must be compatible with the substances to be examined. Liquids used in biochemical examinations are for example blood, urine, water, alcohols or other solvents. Substances which, for example, are intended to be analyzed or detected by biochemical devices are for example proteins, DNA or antibodies. These must not be influenced or modified by the materials used.

Possible materials to be used for the support body 1 are hard polymers, which for the sake of simple production should be processable by injection molding technology. The material should be plastic, i.e. difficult to deform or undeformable. Such materials are provided, for example, by polycarbonate or polypropylene. In a prefabricated mold, the support body 1 of a chip card would be produced with its first recess 4 and second recess 3 in one operation by injection molding technology. In a second operation, the elastomer compound 2 would be introduced into the second recess by injection molding technology. Thermoplastic elastomers, in particular, are suitable as possible materials for the elastomer compound 2. One example of a particularly highly suitable thermoplastic elastomer is a mixture of polypropylene and ethylene propylene diene M-class elastomer, which is known by the brand name Santoprene®.

A chip with a sensor array can be inserted from the rear side 11 into the support body 1, which can be contacted and read out from the rear side by a reader unit 7. The front side of the support body 1, on which the flow channels 4' and reaction chambers are arranged, may be fully covered in a sterile fashion with the aid of a self-adhesive film. This provides gas- and liquid-tight flow channels 4' and reaction chambers.

One possible material for a film is polyethylene. It is, however, also possible to use other film materials.

Figure 2A:
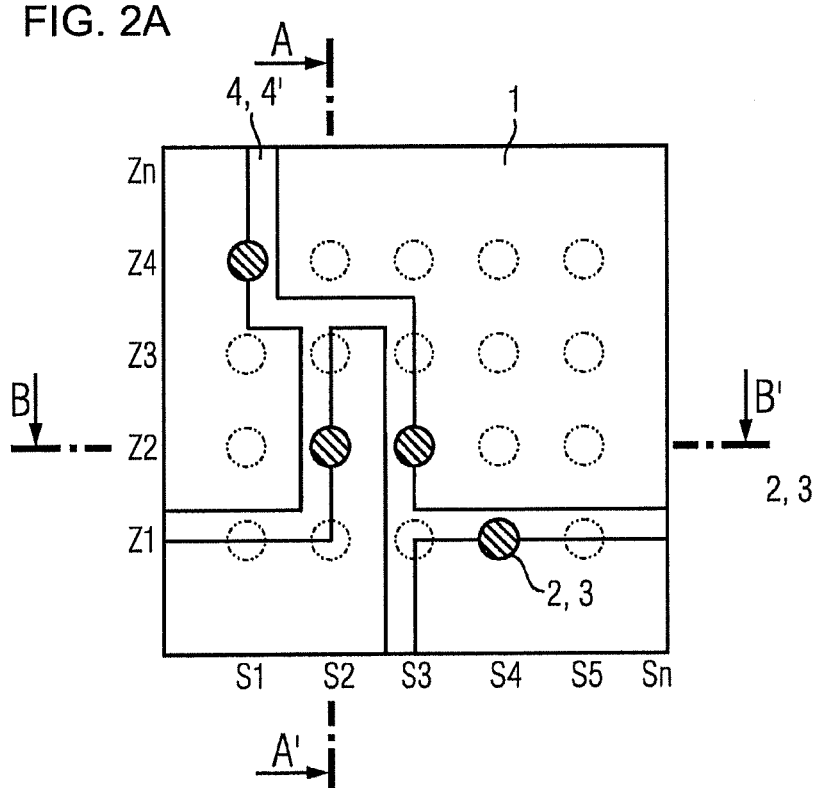
FIGS. 2A-2C are a plan and two sectional views of a device for controlling fluid flows in lab-on-a-chip systems along the section line A-A' and along the section line B-B' in FIG. 2A with an instrument for controlling the valves.
Figure 2B:
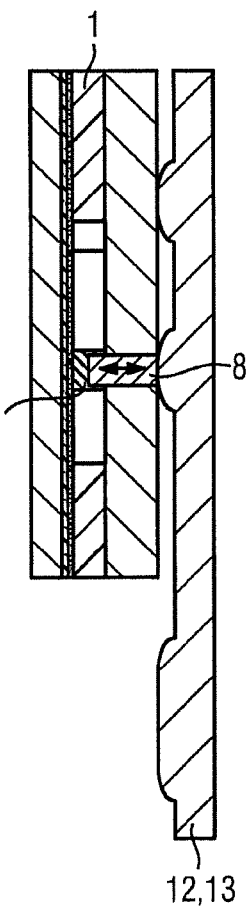
Figure 2C:
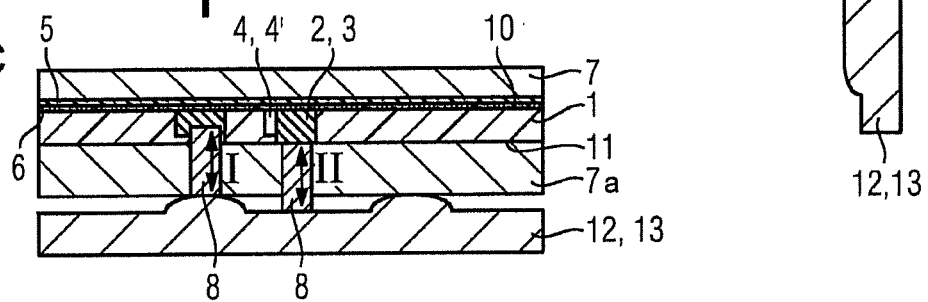

FIG. 2 represents a device for controlling fluid flows in lab-on-a-chip systems in a plan view and in sectional representations along the section line A-A' and along the section line B-B' with an instrument for controlling the valves. The support or substrate body 1 with the valves is fastened in a sandwich fashion in a reader unit 7. Parts of the reader unit 7 are pressed against the front side 10 and against the rear side 11 of the body 1. The body 1 is thereby mounted immobile in the reader unit 7. If the body 1 is configured in the form of a chip card with an electrical chip, then the reader unit 7 can read out and process signals of the sensor array. A valve can be actuated by the reader unit 7 in order to control fluidic processes and chemical reactions in the first recess 4 of the body 1.

As shown in FIG. 2 in the section B-B', two valves, which are represented by way of example for the functionality of the valves, are arranged in the support or substrate body 1. Plungers 8 can put the valves into an open state (right-hand valve I) or a closed state (left-hand valve II). A first recess 4, or a flow channel 4', can be closed in a liquid-tight and/or gas-tight fashion by actuating a valve. A plunger 8, which is arranged in the reader unit 7 and is controlled by the latter, exerts a pressure force from the rear side 11 on the elastomer compound 2. This is done by moving the plunger 8 in the direction of the elastomer compound 2. The pressure force, which is exerted by the plunger 8 on the elastomer compound 2, causes deformation of the elastomer. Since the elastomer can only expand in the direction of the first recess 4, it is pressed into the first recess 4. This continues until the first recess 4 is fully filled with elastomer along a cross section of the first recess 4.

This in turn causes the valve to be closed.

If the plunger 8 is moved away from the elastomer compound 2, then less to no pressure force acts on the elastomer so that the elastomer returns to its original shape. The elastomer is retracted from the first recess and therefore frees it. The valve is opened again.

For simultaneous actuation of the valves, the plungers 8 are fastened on a fixed plate 7a of the reader unit 7. The fixed plate 7a lies on the rear side 11 of the plastic body 1. The plungers 8 are prestressed to opening of the valves by a spring (not shown) so that they exert no pressure on the valves in this state. A plane plate with elevations 12 is arranged movably behind the fixed plate 7a of the reader unit 7. "Behind the fixed plate 7a" refers to that side of the fixed plate 7a which lies on the other side from the body 1. If an elevation of the mobile plane plate 12 lies immediately behind i.e. in contact with a plunger 8, then the latter is pressed in the direction of the elastomer compound 2 of the associated valve and the valve is closed. If there is no elevation of the mobile plane plate 12 behind a plunger 8, then the plunger is pressed, or prestressed, by the spring in the direction of the mobile plane plate 12 and exerts no pressure on the elastomer 2. The valve associated with the plunger 8 is opened.

The mobile plane plate with elevations 12, in conjunction with the reader unit 7, especially the fixed plate 7a of the reader unit 7 with plungers 8, provides the instrument for actuating or controlling the valves 13. The mobile plane plate with elevations 12 and the fixed plate 7a of the reader unit 7, as well as the plungers 8, are generally made of a metal, for example steel, for stability reasons. Nevertheless, other solid materials such as hard plastic may also be used. The springs are generally made of spring steel.

Simultaneous actuation or non-actuation of all the valves of the array of valves according to a predetermined program is carried out by the instrument for actuating the valves 13 and, in particular, by the essentially plane plate 12. When the mobile plane plate with elevations 12 is moved relative to the fixed plate 7a of the reader unit and therefore relative to the plastic body 1 with the valves, valves below which an elevation is inserted during the movement are actuated according to the arrangement of the elevations on the plate 12. If a region of the plate 12 without an elevation is inserted below a valve, the valve remains open. If an elevation lying below a valve is moved away from below the valve and a region of the plate 12 is inserted below the valve in its place, the valve is opened.

By the arrangement of the valves in rows $Z_n$ and columns $S_m$ and the elevations in rows $Z_{n'}$ and columns $S_{m'}$, the spacing of the rows of the elevations being equal to the spacing of the columns of the valve array, and by movement of the plate 12 along a direction which is parallel to a column, all the valves are actuated simultaneously according to a set program. Since only one valve is arranged in each column $S_m$, an elevation only actuates a valve once. With a fixed predetermined arrangement of the valves, the program is determined by the arrangement of the elevations. A program step is determined by $Z_{n'}=Z_n$ columns. When the plate 12 is moved through the spacing of a row, the next program step is carried out according to the arrangement of the elevations in the next row. If a valve is intended to remain closed between two program steps, then an elevation must be formed continuously along a column $S_{n'}$ between two rows.

With uniform movement of the plate 12, with a fixed predetermined spacing of the rows of the valves $Z_n$, the duration of a program step for a predetermined constant speed of advance of the plate 12 relative to the plate 7a is determined by the spacing of the rows of the elevations $Z_{n'}$. As an alternative, however, with predetermined spacings of the rows of the elevations $Z_{n'}$, the speed of advance may be varied according to the desired duration of a process step.

As represented in FIG. 2 in the plan view, the valves are arranged only at particular points of the array of valves. Each column $S_m$ has only one valve. An appropriate number of valves are arranged in a row $Z_n$ according to the chemical reactions to be carried out and the desired microfluidics. The flow channels and reaction chambers, the latter not being represented for the sake of simplicity, are formed as recesses in the front side 10 of the plastic body 1 according to the arrangement of the valves. Complex chemical or biochemical reactions can thus be controlled easily by the method described above. The program, which controls the fluid flows by controlling the valves, is determined by the arrangement of the elevations on the plate 12. For the sake of simplicity, the valves in FIG. 2 are arranged with equal spacings from one another in the columns $S_n$ and rows $Z_m$ in the body 1. The valves are all simultaneously controlled, i.e. actuated or not actuated, by the movement of the plate 12.

Other embodiments, which are not represented in the figures, for example with different spacings of the valves from one another in the columns $S_n$ and rows $Z_m$ in the support or substrate body 1 made of plastic material, may likewise be implemented. Control of the plungers 8 by the plate 12 may also be carried out using indentations instead of elevations in the plate 12. In this case, an indentation corresponds to opening of a valve. It is also conceivable for the plungers 8 not to be prestressed so as to exert no pressure on a valve, but instead for them to be pressed onto the body 1 in the prestressed state or not prestressed at all. A reduced pressure may then contribute to movement of the plungers 8 over the plate 12.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide v. DIRECTV*, 358 F3d 870, 69 USPQ2d 1865 (Fed. Cir. 2004).

What is claimed is:

1. A device for controlling fluid flows in a lab-on-a-chip-system, comprising:
    a chip card having flow channels,
    multiple valves for controlling flow through the flow channels, and
    an instrument to actuate the valves,
        wherein the chip card is arranged in sandwich fashion in or with the instrument,
        wherein said instrument comprises spaced projections,
        wherein selected ones of said valves are opened simultaneously by a linear movement of said instrument for moving the projections relative to said chip card,
        wherein the instrument comprises an essentially planar plate having said projections extending a planar surface of the plate, and wherein said planar plate is moveable parallel to said apertured plate so as to change which valve members are aligned with a projection for changing which valves are closed by movement of a projection thereagainst.

2. The device for controlling fluid flows in a lab-on-a-chip-system according to claim 1, wherein the chip card comprises an electrochemical sensor area for the detection of biochemical substances.

3. A device for controlling fluid flows in a lab-on-a-chip-system, comprising:
a chip card having flow channels,
multiple valves for controlling flow through the flow channels, and
an instrument to actuate the valves,
wherein the chip card is arranged in sandwich fashion in or with the instrument,
wherein said instrument comprises spaced projections,
wherein selected ones of said valves are opened simultaneously by a linear movement of said instrument for moving the projections relative to said chip card,
wherein said valves comprise valve members,
wherein the valve members are in an apertured plaid that is arranged on a side of the chip card,
wherein the instrument comprises an essentially planar plate having said projections extending from a planar surface of the plate, and wherein the essentially planar plate is arranged on an opposite side of said apertured plate from said chip card and has spaced projections extending from a planar surface of the essentially planar plate.

4. The device for controlling fluid flows in a lab-on-a-chip-system according to claim 3, wherein the chip card comprises an electrochemical sensor area for the detection of biochemical substances.

5. A device for controlling fluid flows in a lab-on-a-chip-system, comprising:
a chip card having flow channels,
multiple valves for controlling flow through the flow channels, and
an instrument to actuate the valves,
wherein the chip card is arranged in sandwich fashion in or with the instrument,
wherein said instrument comprises spaced projections,
wherein selected ones of said valves are opened simultaneously by a linear movement of said instrument for moving the projections relative to said chip card,
wherein the instrument comprises an essentially planar plate having said projections extending from a planar surface of the plate, and wherein the essentially planar plate forms a rigid or integral component with the projections.

6. The device for controlling fluid flows in a lab-on-a-chip-system according to claim 5, wherein said valves comprise valve members.

7. The device for controlling fluid flows in a lab-on-a-chip-system according to claim 6, wherein the valve members are in an apertured plate that is arranged on a side of the chip card.

8. The device for controlling fluid flows in a lab-on-a-chip-system according to claim 7, wherein selected ones of said valves are opened in a controlled way by said movement of the projections such that only those valve members that are aligned with a projection are actuated by movement of a projection thereagainst.

9. The device for controlling fluid flows in a lab-on-a-chip-system according to claim 6, wherein selected ones of said valves are opened in a controlled way by said movement of the projections such that only those valve members that are aligned with a projection are actuated by movement of a projection thereagainst.

10. The device for controlling fluid flows in a lab-on-a-chip-system according to claim 5, wherein the chip card comprises an electrochemical sensor area for the detection of biochemical substances.

11. A device for controlling fluid flows in a lab-on-a-chip-system, comprising:
a chip card having flow channels,
multiple valves for controlling flow through the flow channels, and
an instrument to actuate the valves,
wherein the chip card is arranged in sandwich fashion in or with the instrument,
wherein said valves comprise valve members in an apertured plate that is arranged on a side of the chip card,
wherein said instrument comprises an essentially planar plate arranged on an opposite side of said apertured plate from said chip card and linearly movable for actuating said valves,
wherein selected ones of said valves are opened simultaneously in a controlled way by a movement of the essentially planar plate relative to said apertured plate.

12. The device for controlling fluid flows in a lab-on-a-chip-system according to claim 11, wherein the essentially planar plate has spaced projections extending from a planar surface of the plate for actuating the valves or valve members.

13. The device for controlling fluid flows in a lab-on-a-chip-system according to claim 12, wherein selected ones of said valves are opened in a controlled way by a movement of the essentially planar plate relative to said chip card such that only those valve members that are aligned with a projection are closed by movement of a projection thereagainst.

14. The device for controlling fluid flows in a lab-on-a-chip-system according to claim 11, wherein the chip card comprises an electrochemical sensor area for the detection of biochemical substances.

15. A device for controlling fluid flows in a lab-on-a-chip-system, comprising:
a chip card having flow channels,
multiple valves for controlling flow through the flow channels,
an instrument to actuate the valves, and
a reader unit,
wherein the chip card is arranged in sandwich fashion in the reader unit,
wherein selected ones of said valves are opened mechanically and simultaneously by a linear movement of the instrument relative to said chip card,
wherein said instrument comprises multiple projections for mechanically actuating the valves when moving the instrument relative to the chip card,
wherein the instrument comprises an essentially planar plate supporting or forming the projections.

16. The device for controlling fluid flows in a lab-on-a-chip-system according to claim 15, wherein the reader unit comprises parts for being pressed against a front and side of the chip card for immobilizing the chip card in the reader unit.

17. The device for controlling fluid flows in a lab-on-a-chip-system according to claim 15, wherein the chip card comprises an electrical sensor area for the detection of biochemical substances and wherein the reader unit is adapted to read out process signals of the sensor area.

18. The device for controlling fluid flows in a lab-on-a-chip-system according to claim 15, wherein the reader unit is adapted to control fluidic processes and chemical reactions on the chip card by actuating the valves.

19. The device for controlling fluid flows in a lab-on-a-chip-system according to claim 15, wherein the essentially planar plate forms a rigid or integral component with the projections.

\* \* \* \* \*